United States Patent [19]
Gasson

[11] Patent Number: 5,851,171
[45] Date of Patent: Dec. 22, 1998

[54] CATHETER ASSEMBLY FOR CENTERING A RADIATION SOURCE WITHIN A BODY LUMEN

[75] Inventor: Jonathan G. Gasson, Cupertino, Calif.

[73] Assignee: Advanced Cardiovascular Systems, Inc., Santa Clara, Calif.

[21] Appl. No.: 963,883

[22] Filed: Nov. 4, 1997

[51] Int. Cl.⁶ ............................ A61M 25/10; A61N 5/00
[52] U.S. Cl. .................................................. 600/3
[58] Field of Search .................. 600/1–8; 604/104–107, 604/281

[56] References Cited

U.S. PATENT DOCUMENTS

| | | |
|---|---|---|
| 4,697,575 | 10/1987 | Horowitz . |
| 4,706,652 | 11/1987 | Horowitz . |
| 4,748,982 | 6/1988 | Horzewski et al. . |
| 4,762,130 | 8/1988 | Fogarty et al. . |
| 4,763,671 | 8/1988 | Goffinet . |
| 4,771,778 | 9/1988 | Mar . |
| 4,775,371 | 10/1988 | Mueller, Jr. . |
| 4,815,449 | 3/1989 | Horowitz . |
| 4,861,520 | 8/1989 | van't Hooft et al. . |
| 4,940,064 | 7/1990 | Desai ...................................... 607/122 |
| 4,969,863 | 11/1990 | van't Hooft et al. . |

(List continued on next page.)

FOREIGN PATENT DOCUMENTS

| | | |
|---|---|---|
| 0 633 041 A1 | 1/1995 | European Pat. Off. . |
| 0 688 580 A1 | 12/1995 | European Pat. Off. . |
| 4 315 002 | 5/1993 | Germany . |
| WO 92/17236 | 10/1992 | WIPO . |
| WO 93/04735 | 3/1993 | WIPO . |
| WO 94/25106 | 11/1994 | WIPO . |
| WO 95/19807 | 7/1995 | WIPO . |
| WO 95/26681 | 10/1995 | WIPO . |
| WO 96/10436 | 4/1996 | WIPO . |
| WO 97/37715 | 10/1997 | WIPO . |
| WO 97/40889 | 11/1997 | WIPO . |
| WO 98/01183 | 1/1998 | WIPO . |
| WO 98/01185 | 1/1998 | WIPO . |

OTHER PUBLICATIONS

Lindsay, et al., Aortic Arteriosclerosis in the Dog After Localized Aortic X–Irradiation, *Circulation Research,* vol. X, Jan. 1962.

Friedman, et al.,The Antiatherogenic Effect of Iridium$^{192}$ Upon the Coloesterol–Fed Rabbit, *Journal of Clinical Investigation,* 1964.

Friedman, et al., Effect of Iridium$^{192}$ Radiation on Thromboatherosclerotic Plaque in the Rabbit Aorta,*Arch Path,* vol. 80, Sep. 1965.

Hoopes, et al., Intraoperative Irradiation of the Canine Abdominal Aorta and Vena Cava, *Int'l Journal of Radiation Oncology, Biology, Physics,* vol. 13, No. 5, May 1987.

(List continued on next page.)

*Primary Examiner*—John P. Lacyk
*Assistant Examiner*—Samuel Gilbert
*Attorney, Agent, or Firm*—Fulwider Patton Lee & Utecht, LLP

[57] ABSTRACT

The invention is directed to a catheter assembly with blood perfusion capability suitable for maintaining patency of a body lumen for a period of time sufficient to allow delivery of a radiation source to the body lumen. The catheter assembly includes an inner tubular member which extends coaxially within an outer tubular member, with the distal ends of the inner and outer tubular members being joined together. The catheter includes an expandable region which maintains and centers a radiation source within the body lumen while not inhibiting blood to perfuse around and past the expandable region. In one embodiment, the expandable region includes a plurality of outwardly extendable strap-like members which are formed on the outer tubular member of the elongated catheter body. A plurality of the strap-like members can be spaced in a staggered arrangement along the outer tubular member so that when moved to an expanded position, the strap-like members center the radiation source wire within the body lumen.

12 Claims, 3 Drawing Sheets

U.S. PATENT DOCUMENTS

| | | |
|---|---|---|
| 4,976,720 | 12/1990 | Machold et al. . |
| 4,983,167 | 1/1991 | Sahota . |
| 4,998,917 | 3/1991 | Gaiser et al. . |
| 5,002,560 | 3/1991 | Machold et al. . |
| 5,015,230 | 5/1991 | Martin et al. . |
| 5,032,113 | 7/1991 | Burns . |
| 5,034,001 | 7/1991 | Garrison et al. . |
| 5,059,166 | 10/1991 | Fischell et al. . |
| 5,061,273 | 10/1991 | Yock . |
| 5,084,002 | 1/1992 | Liprie .......................................... 600/3 |
| 5,176,661 | 1/1993 | Evard et al. . |
| 5,180,368 | 1/1993 | Garrison . |
| 5,199,939 | 4/1993 | Dake et al. . |
| 5,213,561 | 5/1993 | Weinstein et al. . |
| 5,242,396 | 9/1993 | Evard . |
| 5,258,419 | 11/1993 | Rolando et al. . |
| 5,263,963 | 11/1993 | Garrison . |
| 5,267,960 | 12/1993 | Hayman et al. . |
| 5,273,738 | 12/1993 | Matthews et al. . |
| 5,295,959 | 3/1994 | Gurbel et al. . |
| 5,295,960 | 3/1994 | Aliahmad et al. . |
| 5,295,995 | 3/1994 | Kleiman . |
| 5,302,168 | 4/1994 | Hess . |
| 5,306,246 | 4/1994 | Sahatjian et al. . |
| 5,308,356 | 5/1994 | Blackshear, Jr. et al. . |
| 5,350,361 | 9/1994 | Tsukashima et al. . |
| 5,352,199 | 10/1994 | Tower . |
| 5,354,257 | 10/1994 | Roubin et al. . |
| 5,395,333 | 3/1995 | Brill . |
| 5,411,466 | 5/1995 | Hess . |
| 5,456,667 | 10/1995 | Ham et al. . |
| 5,458,572 | 10/1995 | Campbell et al. . |
| 5,484,384 | 1/1996 | Fearnot . |
| 5,503,613 | 4/1996 | Weinberger . |
| 5,503,614 | 4/1996 | Liprie . |
| 5,507,301 | 4/1996 | Wasicek et al. . |
| 5,540,659 | 7/1996 | Teirstein ........................................ 600/3 |
| 5,643,171 | 7/1997 | Bradshaw et al. ........................... 600/3 |
| 5,730,698 | 3/1998 | Fischell et al. . |

OTHER PUBLICATIONS

Weshler, et al., Inhibition by Irradiation of Smooth Muscle Cell Proliferation in the De–Endothelialized Rat Aorta, 21st Meeting –European Society for Radiation Biology, collected in *Frontiers of Radiation Biology,* 1988.

Dawson, John T., Theoretic Considerations Regarding Low–Dose Radiation Therapy for Prevention of Restenosis After Angioplasty, *Texas Heart Institute Journal,* vol. 18, No. 1, 1991.

Johnson, M.D., et al., Review of Radiation Safety in the Cardiac Catheterization Laboratory, *Catheterization and Cardiovascular Diagnosis,* 1992.

Schwartz, M.D., et al., Effect of External Beam Irradiation on Neointimal Hyperplasia After Experimental Coronary Artery Injury, *Journal of the American College of Cardiology,* vol. 19, No. 5, Apr. 1992.

March, M.D., et al., 8–Methoxypsoralen and Longwave Ultraviolet Irradiation Are a Novel Antiproliferative Combination for Vascular Smooth Muscle, Krannert Institute of Cardiology, Sep. 1992.

Hunink, M.D., et al., Risks and Benefits of Femoropopliteal Percutaneous Balloon Angioplasty, *Journal of Vascular Surgery,* vol. 17, No. 1, Jan. 1993.

Weintraub, M.D., et al., Can Restenosis After Coronary Angioplasty be Predicted From Clinical Variables?, *Journal of the American College of Cardiology,* vol. 21, No. 1, Jan. 1993.

Kuntz, M.D., et al., Generalized Model of Restenosis After Conventional Balloon Angioplasty, Stenting and Directional Atherectomy, *Journal of the American College of Cardiology,* vol. 21, No. 1, Jan. 1993.

Haude, M.D., Quantitative Analysis of Elastic Recoil After Balloon Angioplasty and After Intracoronary Implantation of Balloon–Expandable Palmaz–Schatz Stents, *Journal of the American College of Cardiology,* vol. 21, No. 1, Jan. 1993.

Schwartz, et al., Differential Neointimal Response to Coronary Artery Injury in Pigs and Dogs, Implications for Restenosis Models, *Arteriosclerosis and Thrombosis,* vol. 14, No. 3, Mar. 1994.

Liermann, et al., Prophylactic Endovascular Radiotherapy to Prevent Intimal Hyperplasia After Stent Implantation in Femoropopliteal Arteries, *CardioVascular and Interventional Radiology,* (1994).

Wiedermann, et al., Effects of High–Dose Intracoronary Irradiation on Vasomotor Function and Smooth Muscle Histopathology, *Intracoronary Irradiation and Vasomotion,* Jan. 1994.

Wagner, et al., Potential Biological Effects Following High X–Ray Dose Interventional Procedures, *Journal of Vascular and Interventional Radiology,* Jan.–Feb. 1994, pp. 71–84.

Wiedermann, M.D., et al., Intracoronary Irradiation Markedly Reduces Restenosis After Balloon Angioplasty in a Porcine Model, *Journal of the American College of Cardiology,* vol. 23, No. 6, May 1994.

Kakuta, M.D., et al., Differences in Compensatory Vessel Enlargement, No Intimal Formation, Account for Restenosis After Angioplasty in the Hypercholesterolemic Rabbit Model, *Circulation Research,* vol. 89, No. 6, Jun. 1994.

Fischell, M.D., et al., Low–Dose, β–Particle Emission from 'Stent' Wire Results in Complete, Localized Inhibition of Smooth Muscle Cell Proliferation, *Circulation Research,* vol. 90, No. 6, Dec. 1994.

Waksman, M.D., et al., Endovascular Low–Dose Irradiation Inhibits Neointima Formation After Coronary Artery Balloon Injury in Swine: A Possible Role for Radiation Therapy in Restenosis Prevention, *Circulation Research,* vol. 91, No. 5, Mar. 1, 1995.

Wiederman, M.D., Intracoronary Irradiation Markedly Reduces Neointimal Proliferation After Balloon Angioplasty in Swine: Persistent Benefit at 6–Month Follow–Up, *Journal of the American College of Cardiology,* vol. 25, No. 6, May 1995.

Waksman, M.D., et al., Intracoronary Radiation Before Stent Implantation Inhibits Neointima Formation in Stented Porcine Coronary Arteries, *Circulation Research,* vol. 92, No. 6, Sep. 15, 1995.

Verin, M.D., et al., Intra–Arterial Beta Irradiation Prevents Neointimal Hyperplasia in a Hypercholesterolemic Rabbit Restenosis Model, *Circulation Research,* vol. 92, No. 8, Oct. 15, 1995.

Waksman, M.D., et al., Intracoronary Low–Dose β–Irradiation Inhibits Neointima Formation After Coronary Artery Balloon Injury in the Swine Restenosis Model, *Circulation Research,* vol. 92, No. 10, Nov. 15, 1995.

Hehrlein, C., et al., Radioactive Stents, *Discoveries in Radiation for Restenosis,* Abstract 22 (Jan. 1996).

Fischell, Tim A., M.D., A Beta–Particle Emitting Radioisotope Stent for the Prevention of Restenosis, *Discoveries in Radiation for Restenosis,* Abstract 23 (Jan. 1996).

Li, et al., A Novel Brachyehtapy Source for Treatment of Coronary Artery Restenosis, *Discoveries in Radiation for Restenosis,* Abstract 24 (Jan. 1996).

Waksman, M.D., et al., Catheter–Based Radiation in Stented Arteries, *Discoveries in Radiation for Restenosis,* Abstract 25 (Jan. 1996).

Martin, Louis G., M.D., Radiation for Peripheral Applications: Technical Aspects, *Discoveries in Radiation for Restenosis,* Abstract 27 (Jan. 1996).

Lumsden, M.D., et al., Restenosis in Peripheral Vascular Disease, *Discoveries in Radiation for Restenosis,* Abstract 28 (Jan. 1996).

Schopohl, et al., Endovascular Irradiation for Avoidance or Recurrent Stenosis After Stent Implantation in Peripheral Arteries –5 Years Follow–Up, *Discoveries in Radiation for Restenosis,* Abstract 29 (Jan. 1996).

Waksman, M.D., et al., Radiation in the Peripheral System at Emory, *Discoveries in Radiation for Restenosis,* Abstract 30 (Jan. 1996).

Teirstein, et al., Catheter–Based Radiation Therapy to Inhibit Restenosis Following Coronary Stenting, *Discoveries in Radiation for Restenosis,* Abstract 31 (Jan. 1996).

King III, M.D., et al., Clinical Restenosis Trials Using Beta Energy Radiation, *Discoveries in Radiation for Restenosis,* Abstract 32 (Jan. 1996).

Urban, M.D., et al., Endovascular Irradiation With 90Y Wire, *Discoveries in Radiation for Restenosis,* Abstract 33 (Jan. 1996).

Condado, et al., Late Follow–Up After Percutaneous Transluminal Coronary Angioplasty (PTCA) and Intracoronary Radiation Therapy (ICRT), *Discoveries in Radiation for Restenosis,* Abstract 34 (Jan. 1996).

Weldon, Thomas D., Catheter Based Beta Radiation System, *Discoveries in Radiation for Restenosis,* Abstract 35 (Jan. 1996).

van't Hooft, et al., HDR Afterloader for Vascular Use, *Discoveries in Radiation for Restenosis,* Abstract 36 (Jan. 1996).

Fischell, Robert E., et al., the Radioisotope Stent: Conception and Implementation, *Discoveries in Radiation for Restenosis,* Abstract 37 (Jan. 1996).

Popowski, M.D., et al., Radioactive Wire in a Self–Centering Catheter System, *Discoveries in Radiation for Restenosis,* Abstract 38 (Jan. 1996).

Calfee, Richard V., Ph.D., High Dose Rate Afterloader System for Endovascular Use –Neocardia, *Discoveries in Radiation for Restenosis,* Abstract 39 (Jan. 1996).

Smith, Dr. Edward F., III, Issues on Handling Radioactive Devices to Prevent Restenosis, *Discoveries in Radiation for Restenosis,* Abstract 40 (Jan. 1996).

Unterberg, et al., Reduced Acute Thrombus Formation Results in Decreased Neointimal Proliferation After Coronary Angioplasty, collected in *Discoveries in Radiation for Restenosis –Selected Literature* (Jan. 1996).

Schwartz, et al., Effect of External Beam Irradiation on Neointimal Hyperplasia After Experimental Coronary Artery Injury, collected in *Discoveries in Radiation for Restenosis –Selected Literature* (Jan. 1996).

Hehrlein, et al., Low–Dose RadioactiveEndovascular Stents Prevent Smooth Muscle Cell Proliferation and Neointimal Hyperplasia in Rabbits, collected in *Discoveries in Radiation for Restenosis –Selected Literature* (Jan. 1996).

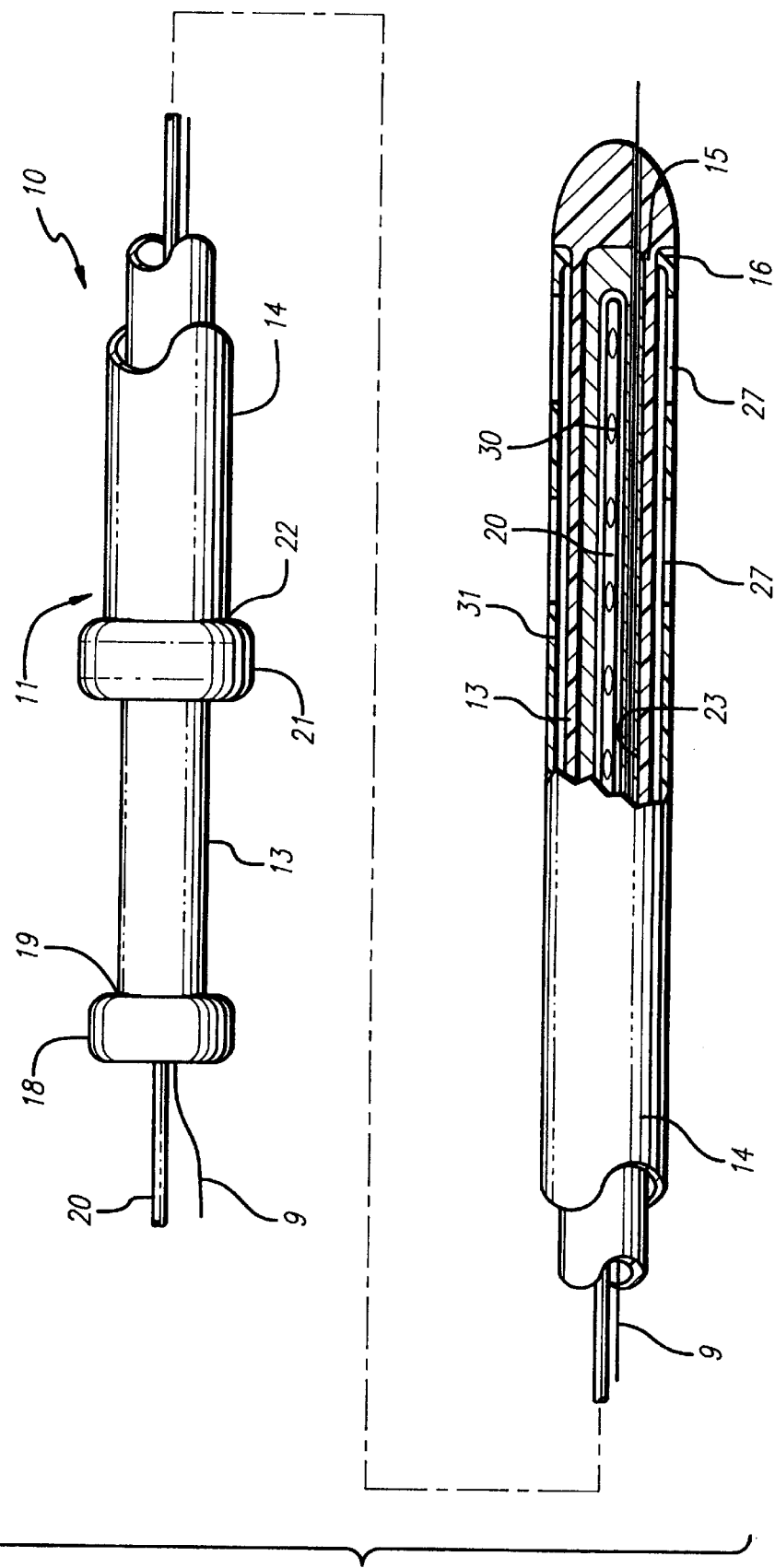

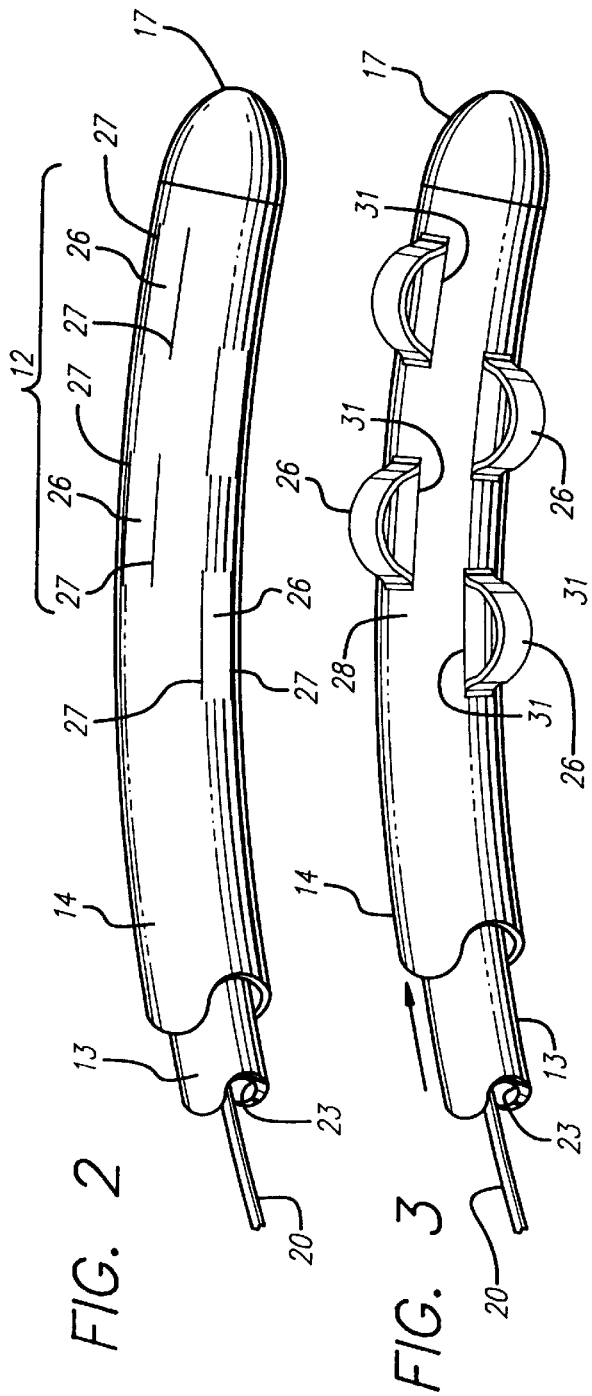
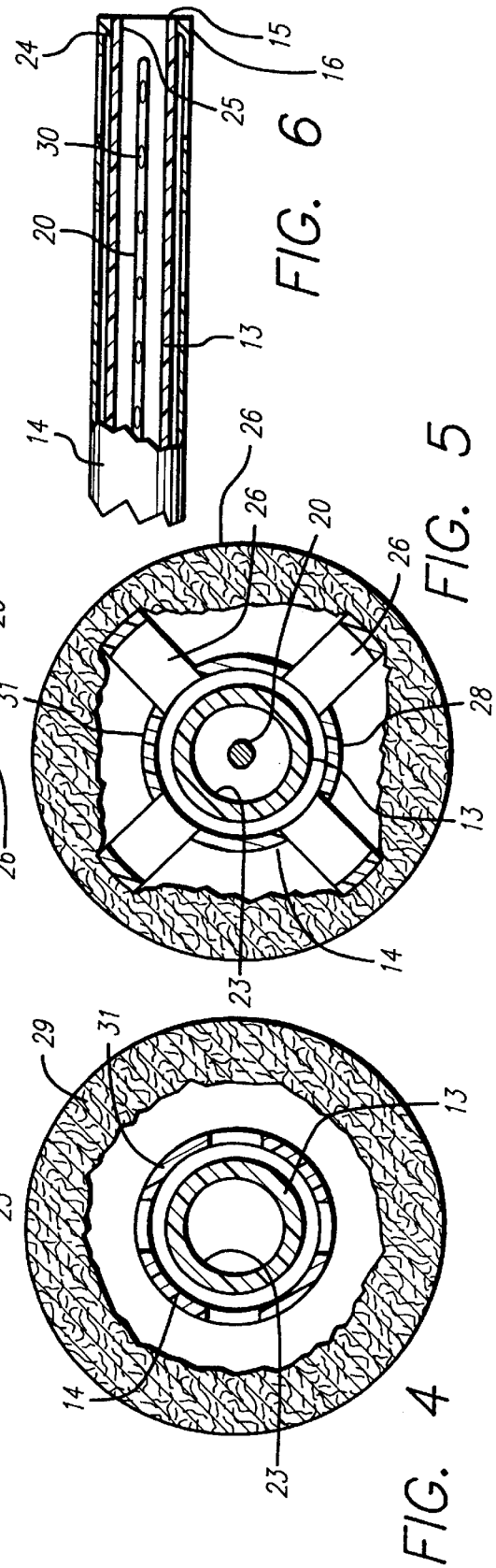

CATHETER ASSEMBLY FOR CENTERING A RADIATION SOURCE WITHIN A BODY LUMEN

BACKGROUND OF THE INVENTION

This invention generally relates to intravascular catheters and particularly to an intravascular catheter assembly for delivering radiation treatment to a body lumen while continuously premitting blood perfusion through the body lumen past and around the catheter assembly.

In percutaneous transluminal coronary angioplasty (PTCA) procedures, a guiding catheter having a preshaped distal tip is percutaneously introduced into the cardiovascular system of a patient through the brachial or femoral artery and is advanced therein until the preshaped distal tip is disposed within the aorta adjacent to the ostium of the desired coronary artery. The guiding catheter is then twisted and torqued from its proximal end to turn its distal tip so that it can be guided into the coronary ostium. In a rapid exchange or an over-the-wire dilatation catheter system, the guide wire and the dilatation catheter having an inflatable balloon on a distal end thereof are introduced into, and advanced through, the proximal end of the guiding catheter to the distal tip of the guiding catheter seated within the coronary ostium. The distal tip of the guide wire is usually manually shaped (i.e. curved) by the physician or one of the attendants before it and the dilatation catheter are introduced into the guiding catheter. The guide wire is usually first advanced out of the distal end of the guiding catheter and is maneuvered into the patient's coronary vasculature containing the stenosis to be dilated, and is then advanced beyond the stenosis. Thereafter, the dilatation catheter is advanced over the guide wire until the dilatation balloon is positioned across the stenosis. Once the dilatation catheter is in position, the balloon of the catheter is filled with radiopaque liquid at relatively high pressures (e.g., generally about 4–12 atmospheres) to inflate it to a predetermined size (preferably the same as the inner diameter of the artery at that particular location) in order to radially compress the atherosclerotic plaque of the stenosis against the inside of the wall of the artery, thereby increasing the diameter of the occluded area. The balloon can then be deflated so that the catheter can be removed and blood flow resumed through the dilated artery.

One common problem that sometimes occurs after an angioplasty procedure has been performed is the development of restenosis at, or near, the original site of the stenosis. When restenosis occurs, a second angioplasty procedure or even bypass surgery may be required, depending upon the degree of restenosis. In order to reduce the likelihood of the development of restenosis and thereby prevent the need to perform bypass surgery or subsequent angioplasty procedures, various devices and procedures have been developed for preventing restenosis after arterial intervention. For example, intravascular stents are commonly implanted to help in the body lumen to help prevent the development of restenosis.

More recent devices and procedures for preventing restenosis after arterial intervention employ the use of a radiation source to prevent the proliferation of smooth muscle cells which are believed to be a contributing cause of restenosis. Balloon catheters have been used to deliver and maintain the radiation source in the area where arterial intervention has taken place, exposing the area to a sufficient radiation dose to abate cell growth. Two devices and methods are described in U.S Pat. No. 5,302,168 (Hess) and U.S. Pat. No. 5,503,613 (Weinberger). Other devices and methods which utilize radiation treatment delivered by an intravascular catheter are disclosed in commonly-owned and assigned co-pending application U.S. Ser. No. 08/654,698, filed May 29, 1996, entitled Radiation-Emitting Flow-Through Temporary Stent and co-pending application Ser. No. 08/705,945, filed Aug. 29, 1996, entitled Radiation Dose Delivery Catheter with Reinforcing Mandrel, which are incorporated herein by reference. Another medical device for the treatment of a body vessel by radiation is disclosed in European Patent App. 0 688 580 A1 (Schneider).

One problem common to many of the balloon catheters which provide radiation treatment to a particular part of a patient's vascular system is that it is sometimes preferable to treat the target area with a lower radiation dosage over a longer period of time rather than a higher dosage of radiation over a shorter period of time. If conventional balloon catheters are utilized to center the catheter and radiation source in the area of an artery where restenosis is likely to occur to allow delivery of a radiation dose, then the inflated balloon may inhibit or restrict the flow of blood through the artery, which can pose serious risk of damage to tissue downstream from the occluded portion of the artery since the tissue will express a deprivation of oxygenated blood. As a result, the time in which the balloon can remain expanded within the artery would be diminished, effecting the time period in which the radiation dosage can be maintained in the area of the artery where restenosis may occur. Thus, a higher dosage of radiation may have to be administered over a shorter period of time due to the occlusion of the vessel caused by the inflated balloon catheter, which again, may not be as advantageous as providing a lower dosage over a longer period of time.

What has been needed and heretofore generally unavailable in catheters which provide treatment of the body vessel with a radiation source is an intravascular catheter assembly which centers a radiation source in the lumen where restenosis may occur for a period of time sufficient to kill the cells and reduce the likelihood of the development of restenosis while not inhibiting blood to perfuse through the body lumen during the radiation procedure. Such a catheter assembly should be capable of centering the radiation source within the body lumen to more evenly administer the radiation to the surrounding tissue and to prevent or reduce the development of radiation burns or "hot spots" on tissue which is too close to the radiation source. Further, such an intravascular catheter assembly should be relatively easy and inexpensive to manufacture, and capable of being formed in a variety of shapes to allow flexibility in the amount and pattern of expansion and deformation of the expandable region. The present invention satisfies these and other needs as will be described hereinafter.

SUMMARY OF THE INVENTION

The present invention is directed to an intravascular catheter assembly with an expandable region located at the distal end of the catheter body which can be positioned within a body lumen for a sufficient period of time to permit delivery of a radiation source to the body lumen while not inhibiting perfusion of blood through the vessel.

The intravascular catheter assembly in accordance with the present invention includes an elongated catheter body having a proximal end and a distal end. The elongated catheter body is made up of an inner tubular member which extends within an outer tubular member in a coaxial configuration, with the distal ends of the inner and outer tubular members being joined together. A radiation source lumen extends within the inner tubular member from the proximal end of the elongated catheter body to a distal portion where the radiation treatment is to be administered. A separate and conventional guide wire lumen extends through the elongated catheter body to allow a guide wire to be used to advance the elongated catheter body to the target area in the body lumen in an "over-the-wire" embodiment of the present invention. Similarly, a separate and conventional guide wire lumen extends through at least the distal segment of the catheter in a known "rapid exchange" catheter configuration. An expandable region located near the distal end of the elongated catheter body can be expanded to contact a portion of the body lumen to maintain the expandable region in the target area and to center the radiation source within the body lumen while not inhibiting the perfusion of blood past and over the expandable region. Axial movement between the outer tubular member and inner tubular member causes the expandable region to move to an expanded position and to retract back to the unexpanded position.

The expandable region is configured to be flexible so that it can be expanded on a curved portion of a body lumen, such a coronary artery. It is also configured to center a radiation source wire within the radiation source lumen, even if the expandable region is positioned on a curved section of the body lumen. Due to the particular structure of the expandable region, blood to flow past the expandable region is not inhibited so that oxygenated blood is supplied to tissue downstream from the catheter when the expandable region is in the expanded configuration.

In one particular embodiment of the present invention, the expandable region is made from a plurality of outwardly extendable strap-like members which are formed on the outer tubular member of the elongated catheter body. Each strap-like member is created by a pair of lengthwise slits which extend into the wall of the outer tubular member to form a thin strip or belt which is capable of flaring or extending radially outwardly from the surface of the outer tubular member when the outer tubular member is subjected to a compressive axial force. A plurality of these strap-like members can be spaced in a staggered arrangement along the outer tubular member so that when moved to the expanded position, the arrangement of strap-like members will center the expandable region within the body lumen which, in turn, centers the radiation source wire within the body lumen. As a result of centering the radiation source within the body lumen, the radiation therapy can be administered more evenly and the possibility of developing radiation burns or hot spots, which may occur if the radiation source is placed too close to the wall of the body lumen, can be reduced or prevented.

The compressive axial force which is needed to "flare" each strap-like member to its expanded position can be achieved, for example, through relative axial movement between the outer tubular member and inner tubular member. Since the distal ends of the outer and inner tubular members are joined together, relative movement of the proximal ends of the outer and inner members can impart a "compression" (the compressive axial force) on the outer tubular member which causes the strap-like member to move into the expanded position. Since the width (the space between the two lengthwise slits) of each strap-like members is less than the width of the surrounding wall area on the outer tubular member, compression of the outer tubular member causes the strap-like members to move away or flare from the outer surface of the wall. The remaining portion of the tubular member remains stiff and becomes somewhat compressed, but does not flare outward as does the strap-like members. As a result, this composite arrangement creates an expandable region on the catheter body which can be moved between an expanded and unexpanded position by simply moving the proximal end of the inner tubular member relative to the proximal end of the outer tubular member along the length of the catheter body. These and other advantages of the invention will become more apparent from the foregoing detailed description thereof when taken in conjunction with the accompanying exemplary drawings.

BRIEF DESCRIPTION OF THE DRAWINGS

FIG. 1A is an elevational view, partially in cross-section, of an over-the-wire catheter assembly for centering a radiation source within a body lumen embodying features of the invention.

FIG. 2 is an elevational view of the catheter assembly of FIG. 1 depicting the expandable region in the normal unexpanded position.

FIG. 3 is an elevational view of the catheter assembly of FIG. 1 depicting the expandable region in the expanded position.

FIG. 4 is a cross-sectional view of the catheter assembly of FIG. 1 showing the expandable region in the unexpanded position within a body lumen, such as an artery.

FIG. 5 is a cross-sectional view of the catheter assembly of FIG. 1 showing the expandable region fully expanded within a body lumen, such as an artery.

FIG. 6 is a cross-section view of the distal end of a catheter assembly for centering a radiation source within a body lumen embodying features of the invention.

DETAILED DESCRIPTION OF THE PREFERRED EMBODIMENTS

Figure 1B:
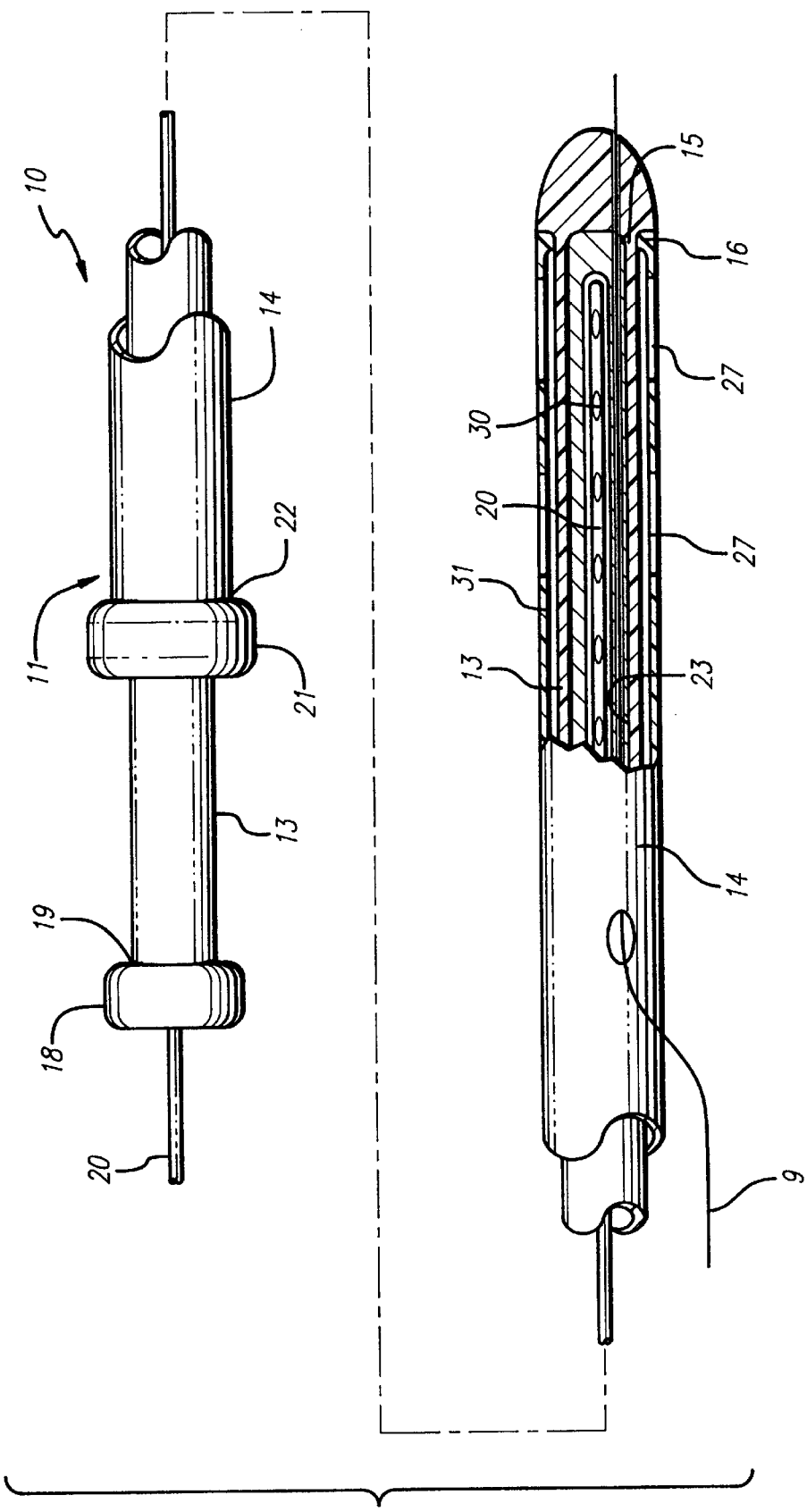
FIG. 1B is an elevational view, partially in cross-section, of a rapid exchange catheter assembly for centering a radiation source within a body lumen embodying features of the invention.

The present invention provides an intraluminal catheter assembly for delivery and maintaining a low dose radiation source to a patient's body lumen, such as a coronary artery or other vessel, for an extended period of time. The catheter assembly does not inhibit perfusion of blood during the radiation therapy and will center the radiation source so that equal amounts of radiation will be applied to the artery. While the invention is described in detail as applied to the coronary arteries, those skilled in the art will appreciate that it can also be used in other body lumens as well, such as peripheral arteries and veins. Where different embodiments have like elements, like reference numbers have been used.

FIG. 1A depicts generally an over-the-wire-type catheter assembly 10 in which guide wire 9 extends through the entire catheter assembly in a known manner. similarly, FIG. 1B depicts generally a rapid-exchange-type catheter assembly 10' in which guide wire 9' extends through at least a distal segment of the catheter in a known manner. Further, details of over-the-wire and rapid-exchange-type catheters can be found in U.S. Pat. Nos. 4,323,071 (Simpson et al.); B1 4323,071; 5,501,227 (Yock); 5,350,395 (Yock); 5,451, 233 (Yock); 5,300,085 (Yock); 5,061,273 (Yock); 5,040,548 (Yock); 5,496,346 (Horzewski et al.); 4,748,982, which are incorporated herein.

In keeping with the invention, FIGS. 1A, 1B, 2 and 3 illustrate a catheter assembly 10 embodying features of the present invention. Catheter assembly 10 (or 10') generally includes an elongated catheter body 11 with an expandable region 12 on the distal portion thereof. The elongated catheter body 11 includes inner tubular member 13 which extends coaxially within outer tubular member 14. The distal end 15 of the inner tubular member 13 is connected to the distal end 16 of the outer tubular member 14 by using suitable means such as adhesives or heat bonding to maintain the ends together. The distal end of the elongated catheter body 11 may include a soft, non-traumatic tip 17 which helps reduce vessel trauma as the catheter assembly 10 is inserted into the body lumen.

A luer fitting 18 is connected to the proximal end 19 of the inner tubular member 13 for receiving a radiation source wire 20. Another fitting 21 is located at the proximal end 22 of the outer tubular member 14 which allows the user to grasp the proximal end 22 of the outer member 14 when the catheter assembly is to be utilized in administering radiation treatment to the body lumen. The inner tubular member 13 includes a radiation source lumen 23 which extends from the proximal end 19 to its distal end 15.

In an alternative embodiment of the catheter assembly, as shown in FIG. 6, the distal end 24 of the elongated catheter body 11 includes an opening 25 which is in communication with the radiation source lumen 23 to allow a guide wire (not shown) to be slidably disposed within the radiation source lumen 23 to facilitate the advancement and withdrawal of the catheter assembly 10 within the body lumen in an "over-the-wire" embodiment of the present invention.

The expandable region 12 is made up of a plurality of individual strap-like members 26 which are formed in the wall portion 31 of the outer tubular member 14. Each strap-like member is formed by a pair of lengthwise slits 27 which extend into the wall of the outer tubular member 14. As can be seen in FIG. 3, these strap-like members 26 are capable of extending radially outwardly (flaring) from the surface 28 of the outer tubular member 14 when a compressive axial force is exerted on the outer tubular member 14 in the area of the expandable region 12. This compressive axial force can be created by moving the proximal end 22 of the outer tubular member 14 relative to the proximal end 19 of the inner tubular member 13. For example, the proximal end 19 of the inner tubular member 13 can be held firmly to prevent the tubular member 13 from moving. Thereafter, the proximal end 22 of the outer tubular member 14 can be grasped by the user and moved in an axial direction (the lengthwise axis of the catheter body) away from the proximal end 19 of the inner tubular member 13. As a result, a compression force is created on the wall of the outer tubular member 14 which causes the strap-like members to extend from the unexpanded position shown in FIG. 2, to the expanded position shown in FIG. 3. The arrow in FIG. 3 shows the direction that the outer tubular member 14 must be moved in order to create this compressive force. In order to retract the strap-like members to the original unexpanded position, the user simply moves the proximal end 22 of the outer tubular member 14 towards the proximal end 19 of the inner tubular member 13.

In a similar fashion, this compressive axial force can be created by maintaining the outer tubular member stationary and moving the proximal end 19 of the inner tubular member away from the proximal end 22 of the outer tubular member 14. In fact, similar results can be obtained by simply moving one or both of the tubular members 13 and 14 relative to the other.

As can be seen in FIGS. 4 and 5, once the catheter assembly 10 has been properly positioned within the body lumen 29, preferably the radiation source wire 20 can be inserted into the radiation source lumen 23 for a period of time sufficient to provide the radiation dosage to the lumen. Preferably, the radiation source wire 20 is hollow at its distal end and contains a radiation dose in the form of a radiation source 30, such as pellets, radiation gas, or radioactive liquid or paste. As an alternative to the radiation source wire, the radiation source can include a radioactive liquid, radioactive powder, radioactive paste, radioactive gas, or radioactive pellets which can be injected into radiation source lumen 23 and then withdrawn after the radiation treatment is completed. The radiation source wire 20 may also have a radioactive source coated on its distal end. This radiation source wire 20 provides the proper doses of radiation to the areas of the artery 29 (or other body lumen) where arterial intervention has been performed, either by PTCA, PTA, atherectomy, stenting or other means to help abate the proliferation of smooth muscle cells in this region. If an embodiment which includes an opening which extends through the distal end of the elongated catheter body for advancing the catheter along a guide wire is used (FIG. 6), a protective sheath (not shown) may have to be used to encase the radiation source wire 20 to prevent the radiation source from being exposed to any bodily fluids, such as blood, and to provide a sterile barrier between the radiation source wire (which can be reusable and is not sterile) and the patient's vascular system. It is preferable that the radiation source wire be stored and its deployment controlled by an afterloader (not shown) which is known in the art. The luer fitting 18 of the inner tubular member 13 would be connected to such an afterloader to allow the radiation source wire 20 to be placed into the radiation source lumen 23.

In practice, once the catheter assembly 10 has been placed within the vasculature of the patient, the expandable region of the catheter body is usually not centered in the body lumen, as is shown in FIG. 4. Centering can be attained by moving the strap-like members 26 into the expanded position. This is easily performed by moving the proximal end of the outer tubular member relative to the inner member, as described, to create the necessary compressive force which flares the strap-like members to the expanded position as shown in FIG. 5. Thereafter, the radiation source wire 20 (or other radiation source) can be advanced through the radiation source lumen 23 to the target area.

It is noted that reference herein to the "target area" means that part of the body lumen that has received a PTCA, PTA, atherectomy or similar procedure to reduce or remove a stenosis, which is subject to the development of restenosis caused, in part, by intimal hyperplasia or the proliferation of smooth muscle cells.

Once the required period of time for radiation treatment has been completed, the expandable region 12 can be retracted to the normal unexpanded position, allowing the catheter assembly and radiation source wire to be removed from the body lumen.

Generally, the dimensions of the catheter assembly of the present invention are essentially the same dimensions of catheter assemblies used in angioplasty procedures. The overall length of the catheter body may be about 100 to 175 cm when a Seldinger approach through the femoral artery is employed. The diameter of the catheter body may range from about 0.30 to 0.065 inches. The expandable region in the unexpanded condition has approximately the same diameter as the catheter body, but may be expanded to a maximum diameter of about one to about 5 mm for coronary arteries and substantially larger (e.g., 10 mm) for peripheral vessels. The diameter of the guide wire lumen should be sufficiently larger than the diameter of the guide wire to allow the catheter to be easily advanced and removed over the guide wire. Additionally, the diameter of the guide wire should be sufficiently larger than the diameter of the radiation source wire and protective sleeve to allow these two devices to be easily advanced and removed from within the guide wire lumen.

The inner tubular member includes a luer fitting which can be connected to an afterloader (not shown) to allow the radiation source to be stored away from medical personnel until the radiation therapy is to be administered to the target area. For this reason, the length of the inner tubular member may be much longer than the length of the outer tubular member in order to reach the remote afterloader.

The particular size, shape and location of the straplike members can also be varied without departing from the spirit and scope of the present invention. For example, while the two slits which form each strap-like member is shown generally parallel to each other, it is possible to utilize slits which are offset from each other to create strap-like members having sizes and shapes which are quite different from what is shown in the accompanying figures. Such variations to the strap-like members should achieve the same results of creating a composite arrangement of extending members which center and maintain the radiation source within the body lumen. Additionally, the number of strap-like members and their location on the outer tubular member can be varied as well without departing from the spirit and scope of the present invention.

In use, the expandable region is maintained in its expanded position for a time sufficient to allow the radiation dosage to effect those cells which would otherwise cause restenosis to develop. Preferably, a sufficient dose of radiation can be delivered from about one minute to about sixty minutes to prevent development of restenosis. In its expanded condition, the expanded region presses against, or at least comes in close proximity to, the wall of the artery and in doing so centers the radiation source wire within the artery. Centering of this radiation source wire is important so that all portions of the artery receive as close to uniform and equal amounts of radiation as possible. Also, centering helps prevent radiation burns or hot spots from developing on portions of the target area.

The catheter assembly of the present invention as described herein is generally employed after an atherectomy, percutaneous transluminal coronary angioplasty procedure, or stent implantation to allow the radiation dose to be administered to an area where restenosis might otherwise develop within a coronary artery. It should be recognized by those skilled in the art that the catheter of the present invention can be used within a patient's vasculature system after vascular procedures other than a PTCA, stent implantation or atherectomy have been performed.

The catheter assembly of the present invention may be formed from conventional materials of construction which are described in detail in prior art patents referenced herein. The materials forming the inner and outer tubular members of the catheter body and protective sheath can be made out of relatively inelastic materials, such as polyethylene, polyvinyl chloride, polyesters and composite materials. It should be appreciated that since these tubular members are subjected to compressive axial forces, the members should have sufficiently lateral flexibility to withstand the sometimes tortuous path leading to the target area, but retain sufficient stiffness in the axial direction (the lengthwise direction of the catheter body) to allow the compressive force to act on the strap-like members to move them to the expanded position.

The various components may be joined by suitable adhesives such as the acrylonitrile based adhesive sold as Loctite 405. Heat shrinking or heat bonding may also be employed when appropriate. The radiation source wire can be made from materials such as stainless steel, titanium, nickel-titanium and platinum-nickel alloys, or any NiTi alloys, or any polymers and composites. Variations can be made in the composition of the materials to vary properties.

As described herein, the catheter assembly will deliver a prescribed dosage of radiation through the body lumen, such as a coronary artery, and is configured to provide the dosage over longer periods of time if necessary, due to the catheter not inhibiting blood to perfuse past the expanded region during treatment. It is preferred that a low dosage of radiation, on the order of about 0.1 up to about 3.0 curies be the typical radiation dose level provided to treat, for example, a coronary artery. Preferably, 1 to 2 curies will provide a proper dosage level over an appropriate time period.

The radiation delivered to a coronary artery should be in the range from about 20 to 5,000 rads in preferably not less than thirty seconds. The radiation dose can be delivered in less than thirty seconds, however, it is preferable that a longer time frame be used so that a lower dose can be administered in the target area.

It is contemplated that any number of radiation sources be used, and the preferred radiation sources include iridium$^{192}$ phosphorus$^{32}$. Further, it is contemplated that the radiation sources may emit beta particles or gamma particles to affect the target cells. However, alpha emitting radiation sources also can be used even though such radiation does not travel very far in human tissue. The use of beta and gamma emitting radiation sources is well known for treating and killing cancerous cells.

Other modifications can be made to the present invention without departing from the spirit and scope thereof. The specific dimensions, doses, times and materials of construction are provided as examples and substitutes are readily contemplated which do not depart from the invention.

What is claimed is:

1. A radiation centering catheter assembly for maintaining the patency of a body lumen for a period of time sufficient to permit delivery of a radiation dose to the body lumen while permitting blood perfusion, comprising:

an elongated catheter body having a proximal end and a distal end, the elongated catheter body having an inner tubular member with an uninterrupted surface which extends coaxially within an outer tubular member and having the distal ends of the inner and outer tubular members connected together;

a radiation source;

a radiation source lumen at least partially containing the radiation source, extending through at least a portion of the elongated catheter body for receiving the radiation source which emits radioactive particles into the body lumen; and an expandable region having an uninterrupted surface except for a plurality of slits disposed radially and staggered longitudinally, and located near the distal end of the elongated catheter body, the expandable region adapted to be expanded, upon application of a force on the outer tubular member, into contact with a portion of the body lumen and center at least the expandable region of the catheter body within the body lumen so that blood flow past and over the expandable region is not inhibited.

2. The catheter assembly of claim 1, wherein axial movement between the outer tubular member relative to the inner tubular member causes the expandable region to move between an unexpanded position and an expanded position.

3. The catheter assembly of claim 1, wherein the expandable region is made from a plurality of strap-like members formed on the outer tubular member which extend radially outwardly to an expanded position upon application of a force on the outer tubular member.

4. The catheter assembly of claim 3, wherein a pair of slits extend into a wall portion the outer tubular member to form each strap-like member.

5. The catheter assembly of claim 4, wherein the pair of slits extend lengthwise into the wall portion of the outer tubular member to form each strap-like member.

6. The catheter assembly of claim 3, wherein axial movement between the outer tubular member relative to the inner tubular member causes each of the strap-like members to move between an unexpanded position and an expanded position.

7. The catheter assembly of claim 4, wherein the slits extending into the wall portion of the outer tubular member form the size and shape of each strap-like member.

8. The catheter assembly of claim 1, further including a guide wire lumen extending through at least a portion of the elongated catheter body for receiving a guide wire used to advance the elongated catheter body to the area in the body lumen where the radiation dose is to be delivered.

9. The catheter assembly of claim 1, wherein the radiation source lumen is adapted to receive a radiation source taken from the group of radiation sources comprising a radiation source wire, radioactive pellets, a radioactive liquid, a radioactive gas, a radioactive powder, and a radioactive paste.

10. The catheter assembly of claim 1, wherein the radiation source lumen extends within the inner tubular member.

11. The catheter assembly of claim 9, further including a protective sheath adapted to encase the radiation source wire, the protective sheath and radiation source wire being insertable within the radiation source lumen to provide a radiation source to the body lumen.

12. A method for maintaining the patency of a body lumen for a period of time sufficient to permit delivery of a radiation dose to the body lumen while providing for blood perfusion, comprising the steps of:

a) providing a catheter having:
   an elongated catheter body having a proximal end and a distal end, the elongated catheterbody having an inner tubular member with an uninterrupted surface which extends coaxially within an outer tubular member and having the distal ends of the inner and outer tubular members connected together;
   a radiation source lumen extending through at least a portion of the elongated catheter body for receiving a radiation source for irradiating at least a portion of the body lumen; and
   an expandable region having an uninterrupted surface except for a plurality of slits disposed radially and staggered longitudinally, and located near the distal end of the elongated catheter body, wherein the expandable region is expandable upon application of a force on the outer tubular member into contact with a portion of the body lumen and center at least the expandable region of the catheter body within the body lumen while providing for perfusion of blood past and over the expandable region;

b) advancing the catheter assembly until the expandable region is positioned in the body lumen;

c) expanding the expandable region by applying a force on the outer tubular member allowing the expandable region to contact and center at least the radiation source lumen within the body lumen;

d) inserting a radiation source into the radiation source lumen and advancing the radiation source to the desired area in the body lumen to irradiate the body lumen;

e) withdrawing the radiation source;

f) retracting the expandable region; and g) withdrawing the catheter assembly from the body lumen.

* * * * *